United States Patent [19]
Strukel

[11] Patent Number: 5,919,157
[45] Date of Patent: Jul. 6, 1999

[54] SHAPED FLEXIBLE INFUSION SLEEVE

[76] Inventor: Igor Strukel, 141 E. 3rd St., New York, N.Y. 10009

[21] Appl. No.: 09/067,528

[22] Filed: Apr. 28, 1998

[51] Int. Cl.[6] ............................. A61B 17/20; A61B 17/22; A61F 1/00
[52] U.S. Cl. ............................... 604/22; 604/49; 604/268; 604/282; 606/169
[58] Field of Search .................................... 604/22, 49, 51, 604/113, 264, 164, 170, 171, 239, 268, 271, 272, 274, 280, 282, 902; 606/166, 167, 169, 170; 601/2; 600/466

[56] References Cited

U.S. PATENT DOCUMENTS

| | | | |
|---|---|---|---|
| 3,090,384 | 5/1963 | Baldwin et al. | 604/272 |
| 4,406,656 | 9/1983 | Hattler et al. | 604/280 |
| 4,515,583 | 5/1985 | Sorick | 604/22 |
| 5,071,421 | 12/1991 | Stahl | 606/107 |
| 5,084,009 | 1/1992 | Mackool | 604/22 |
| 5,116,310 | 5/1992 | Seder et al. | 604/266 |
| 5,188,589 | 2/1993 | Sypych et al. | 604/22 |
| 5,322,504 | 6/1994 | Doherty et al. | 604/22 |
| 5,562,696 | 10/1996 | Nobles et al. | 604/264 |
| 5,618,267 | 4/1997 | Palestrant | 604/264 |
| 5,728,124 | 3/1998 | Cockburn et al. | 604/22 |
| 5,728,130 | 3/1998 | Ishikawa et al. | 604/22 |
| 5,788,679 | 8/1998 | Gravlee, Jr. | 604/22 |
| 5,830,192 | 11/1998 | Van Voorhis | 604/22 |

*Primary Examiner*—Wynn Wood Coggins
*Assistant Examiner*—Sharon Finkel
*Attorney, Agent, or Firm*—Nims, Howes, Collison, Hansen & Lackert

[57] ABSTRACT

A shaped flexible infusion sleeve provides for delivery of an infusion fluid to the tip of a vibrating needle used in a phacoemulsification procedure for removing cataracts. The shaped flexible infusion sleeve has a non-circular cross-sectional shape which allows deformation yet prevents collapse of the sleeve onto the vibrating needle so as to avoid undesired heating during surgery. The shaped flexible infusion sleeve has at least two constriction points which add sufficient structural stiffness to prevent full collapse of the sleeve once inserted into an incision in the eye, while at the same time providing sufficient flexibility to enhance sealing of the incision.

10 Claims, 3 Drawing Sheets

SHAPED FLEXIBLE INFUSION SLEEVE

TECHNICAL FIELD

This invention relates to ultrasonic surgical devices and more particularly to a shaped flexible infusion sleeve which surrounds an ultrasonic work tip used for ophthalmic surgery.

BACKGROUND

Various types of ultrasonic devices are used for surgical applications, for example, in ophthalmic surgery for removing cataracts and other tissue. These devices employ a hollow work tip to transmit ultrasonic energy which emulsifies tissue which is to be removed by suction through the tip. This method is known as "pharcoemulsification". An incision is made in the eye and the vibratable needle inserted for fracturing a cataract. A suction force is applied through the needle interior withdrawing the fragmented cataract. An infusion sleeve surrounds a portion of the needle and supplies a fluid into the eye which thus assists in flushing and removing the fragmented cataract components. The fluid also serves to cool the vibrating needle so as to prevent heating which can cause tissue damage. In addition, the fluid infusion serves to maintain the eye in an inflated pressurized condition during cataract removal.

One problem that has been encountered with prior art devices is that during cataract surgery, fluid leaks from between the edges of the incision and the exterior surface of the infusion sleeve. Loss of this fluid can cause collapse of certain tissue within the eye which could cause damage.

One type of infusion sleeve that has been used for such surgery is made of silicon. However, this was found unacceptable because, as a soft compressible material, the incision tends to compress the non-rigid silicon sleeve against the vibrating needle which results in relative rubbing movement between the silicon sleeve and the vibrating tip. This generates undesirable heat that can result in burns, and shrinkage of ocular tissues surrounding the compressed silicon sleeve. Further, collapse of the infusion sleeve against the vibrating needle constricts the path of fluid flow into the eye thereby hampering efforts to keep the eye pressurized and inflated.

One method for overcoming this deficiency has been to use infusion sleeves made from rigid non-compressible materials, such as polytetrafluoroethylene (PTFE) or metals. While rigid non-compressible sleeves avoid the collapse problem encountered with the soft sleeves, the typical rigid sleeve does not match the contour of the eye incision and therefore continues to allow for leakage through the edges of the incision.

In U.S. Pat. No. 5,084,009, a rigid infuision sleeve is described which reduces leakage in that the rigid sleeve has a ellipsoidal configuration. In an alternative embodiment, a vibrating needle is surrounded by a rigid circular infusion sleeve which itself is then surrounded by a soft deformable infusion sleeve which is circular in cross section, but which then becomes snug fitted by compression induced by the wound incision to assume approximately the ellipsoidal configuration. Thus, when the silicon sleeve is compressed, it compresses against the inner rigid non-compressible sleeve so as to avoid collapse on the needle.

Utilizing the rigid ellipsoidal configuration sleeve has several disadvantages. In particular, in use, the work tip is frequently inserted and removed several times during the course of a procedure and consequently, the direction of the ellipsoidal configured sleeve is important and must be maintained otherwise, leakage can occur as the needle is manipulated within the incision. For example, if turned 90 degrees this could cause damage to the delicate eye tissue.

Utilizing the second embodiment of the '009 Patent requires an instrument with multiple co-axial components which has an increased diameter, requiring an incision size which is somewhat larger and more difficult for a surgeon to manipulate within the incision.

In U.S. Pat. No. 5,188,589, a textured irrigating sleeve is described which utilizes a circular cross-section and a pebbled or granulated interior surface of a sleeve which, though in contact and contactable with a vibrating needle, does allow some fluid to pass thereby. However, the potential for heating still remains, and also the potential for uneven supply of infusion fluid to the eye. In U.S. Pat. No. 4,808,154, a circular infusion sleeve is described which utilizes at least one internal longitudinally extending rib member to guide a flushing fluid through the cylindrical member and to isolate the interior portions of the cylindrical sleeve from the tip member. In essence, collapse is again allowed between the tip and infusion sleeve, the rib engaging the needle. However, again, this results in heating, requiring a larger diameter sleeve and, with a circular cross section with longitudinal ribs, resists the tendency to assume an ellipsoidal shape when placed in an incision.

SUMMARY OF THE INVENTION

It is an object of the present invention to provide an infusion sleeve which is made of a soft flexible material but which avoids contact with a vibrating tip so as to minimize localized heating and interruption of fluid flow. It is a further object to provide an infusion sleeve which has a uniform wall thickness, but which is sufficiently flexible so as to conform to the shape of the incision, yet is of sufficient rigidity so as prevent collapse once placed within the incision.

These and other objects of the present invention are achieved by a surgical instrument for removing tissue through an incision in a patient's eye, the instrument including a handpiece, a hollow vibratable needle connected to the handpiece, an ultrasonic drive associated with the needle for imparting vibration thereto, the surgical instrument further comprising a hollow compressible infusion sleeve having a proximal portion and a distal portion, the proximal portion connected to the handpiece, the infusion sleeve surrounding a substantial portion of the vibratable needle, the infusion sleeve being co-axial therewith, a fluid passage defined between an outer surface of the needle, and an inner wall surface of the sleeve, the distal end of the sleeve providing a port for delivery of the infusion fluid adjacent a tip of the needle, the infusion sleeve having an uncompressed non-circular shape having at least two constriction points, such that the sleeve is partially deformable to approximate a shape of the incision, the constriction points restricting deformation to prevent complete collapse of the sleeve onto the vibratable needle.

In one embodiment, the shaped infusion sleeve has four constriction points and has the shape of a diamond; in another, three constriction points and the shape of a triangle; in yet another embodiment, the shaped infusion sleeve has two constriction points and has the shape of an arch.

In each case, the constriction points provided by the non-circular shape limit deformation and prevent collapse to the extent that detrimental heating and inhibition of fluid flow would occur. Such a sleeve is simple to manufacture, of small diameter to minimize incision size, yet provides a proper balance between flexibility and directional stiffness to enhance performance during surgery and thereby avoid eye damage.

DETAILED DESCRIPTION OF THE INVENTION

Figure 1:
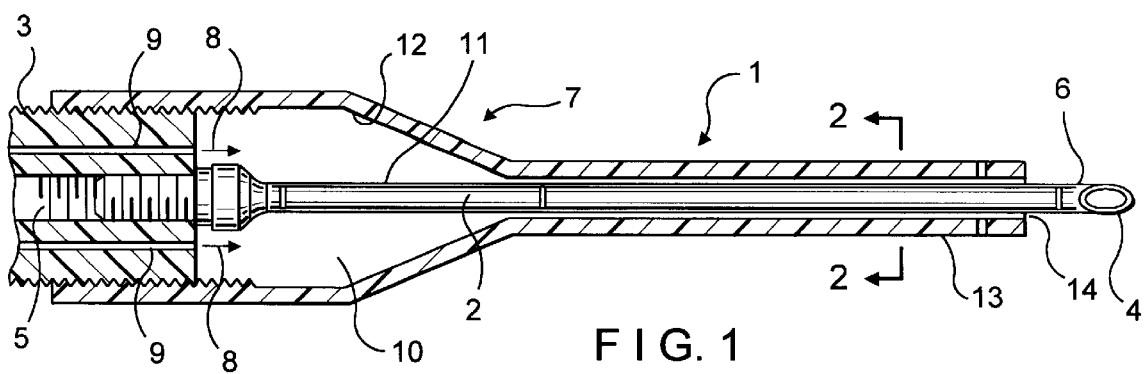
FIG. 1 is a cross-sectional view of a surgical instrument in accordance with the present invention.

Referring to FIG. 1, a cross-sectional view of a surgical instrument 1 for use in preforming the phaceoemulsification of issue in an eye is shown. The instrument is a conventional phaceoemulsification instrument which includes a vibrating needle 2 connected to a handpiece 3. The needle is hollow and has a passage 4 connected to a passage 5 through which vacuum is used to suck out material emulsified by a work tip 6. An infusion sleeve 7 surrounds the needle and is threaded onto and thus also connected to the handpiece. A fluid indicated by arrow 8 is supplied through ducts 9 in the handpiece into a conduit 10 defined by the space between an outer surface 11 of the needle and an inner surface 12 of the sleeve. The fluid is delivered to a distal end 13 of the sleeve which forms a port 14 adjacent to the work tip 6. Thus, fluid is delivered from the handpiece through the passage to the area adjacent the tip so as to enable removal of the fractured cataract through the interior of the hollow vibrating needle.

Figure 2:
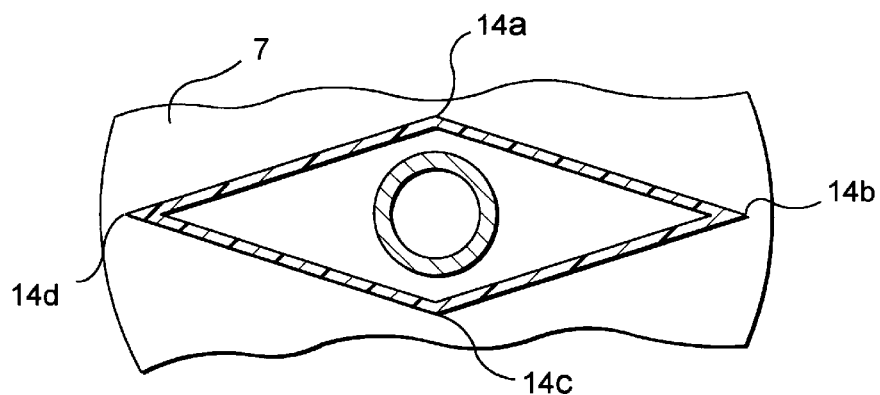
FIG. 2 is an enlarged cross-sectional view taken along line 2—2 of FIG. I of the infusion sleeve having a diamond shape produced in accordance with the present invention.

As seen in FIG. 2, the infusion sleeve 7 is diamond shaped in cross-section. This is achieved by including four constricting points 14a, b, c, and d about the diameter thereof during production of the sleeve, defining four planar surfaces. The purpose in providing a non-circular cross-section, having constriction points is to provide structural support for the sleeve so as to prevent substantial collapse when the sleeve is placed within an incision in the eye.

By having constriction points, supporting structures or walls are defined which provide resistance and direction to the forces acting on the sleeve. By distributing the forces through these structures, deformation is limited to prevent substantial collapse yet sufficient deformation occurs to enhance sealing between the sleeve and adjacent tissue.

Figure 5:
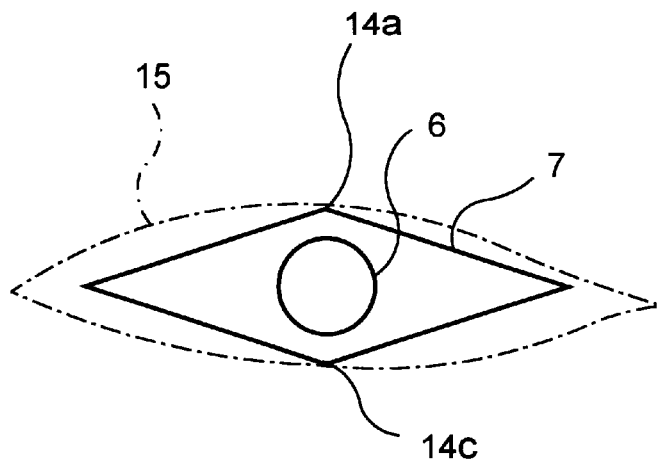
FIG. 5 is a view shape showing the diamond shaped sleeve within an incision.

Referring to FIG. 5, the diamond shaped sleeve 7 is shown placed within an incision 15 in the eye. The upper and lower constricting points 14a and 14c, act in conjunction with the side constricting point 14b and 14d so as to prevent full collapse of the sleeve due to the compression of the tissue on the sleeve. Thus, though some deformation of the sleeve does occur, which enhances the sealing of the sleeve against the tissue, full collapse does not occur and therefore the infusion fluid can still pass about the entire circumference of the needle and rubbing of the needle against the sleeve with consequent heating is avoided.

Figure 3:
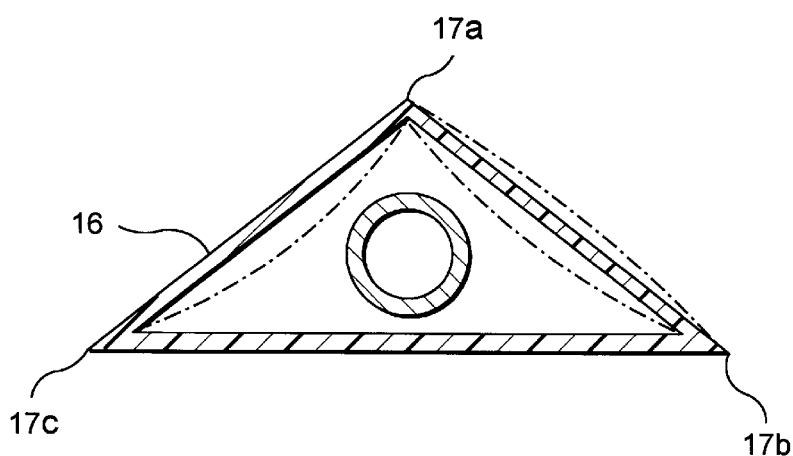
FIG. 3 is a front view of an infuision sleeve having a triangular shape.

Referring to FIG. 3, an infusion sleeve 16 having a triangular shape including three constricting points 17a b and c, is shown. In this embodiment, the upper point 17a of the triangle works in conjunction with the side points 17b and 17c, again to prevent collapse of the sleeve against the vibrating needle and thereby avoid the problems encountered with prior art sleeves. Further, the non-circular diamond shape and triangular shape more closely approximate the actual shape of the incision thereby further enhancing the ability of the sleeve to seal against the incision and prevent fluid leakage, while at the same time preventing collapse of the sleeve onto the vibrating needle.

Figure 6:
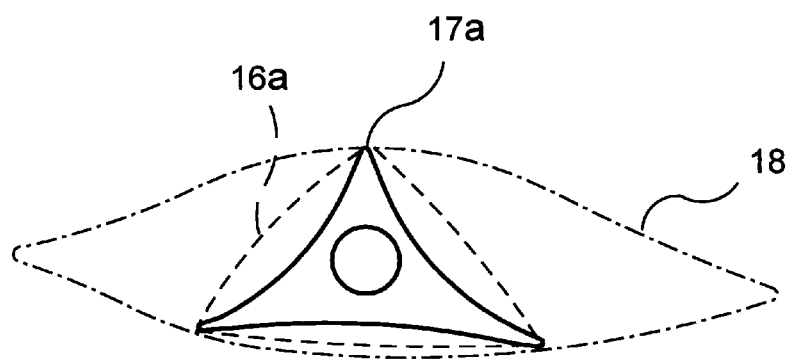
FIG. 6 is a view showing the triangular shape sleeve in an incision.

Referring to FIG. 6, the triangular sleeve is shown placed within an incision 18 with a phantom line 16a showing the uncompressed outline of the sleeve, and the expected deformation by bowing of the sides of the triangle inwardly, due to compression caused by the tissue adjacent the incision. However, this deformation is limited due to the structural stiffness attained by this particular shape, the three planar surfaces defined by the three constriction points preventing collapse. Contact of the sides of the triangle with the vibrating needle is to be avoided.

Figure 4:
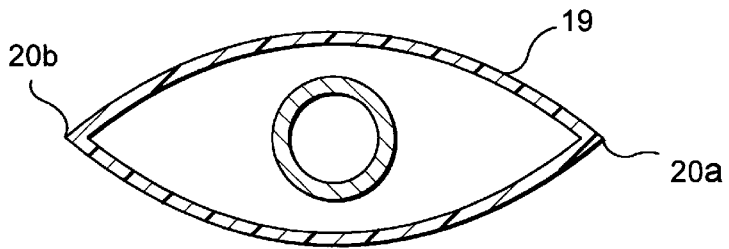
FIG. 4 is a front view of an infusion sleeve having two constriction points producing an arched shape.
Figure 7:
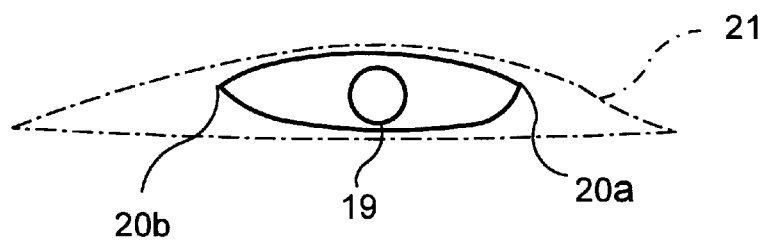
FIG. 7 is a view showing the arch shaped sleeve in an incision.

Referring to FIG. 4, a non-circular cross-section of a sleeve 19 is shown which includes two constricting points 20a and 20b which define a shape approximating a pair of arches. As shown in FIG. 7, the arch shape provides a close approximation to the shape of the actual incision, with the constricting points again resisting collapse of the domed portion of the sleeve when placed within an incision 21. Additionally, this shape provides enhanced fluid flow through the side regions adjacent to the needle, to enhance cooling effectiveness while maximizing the sealing effectiveness of the sleeve.

Figure 8:
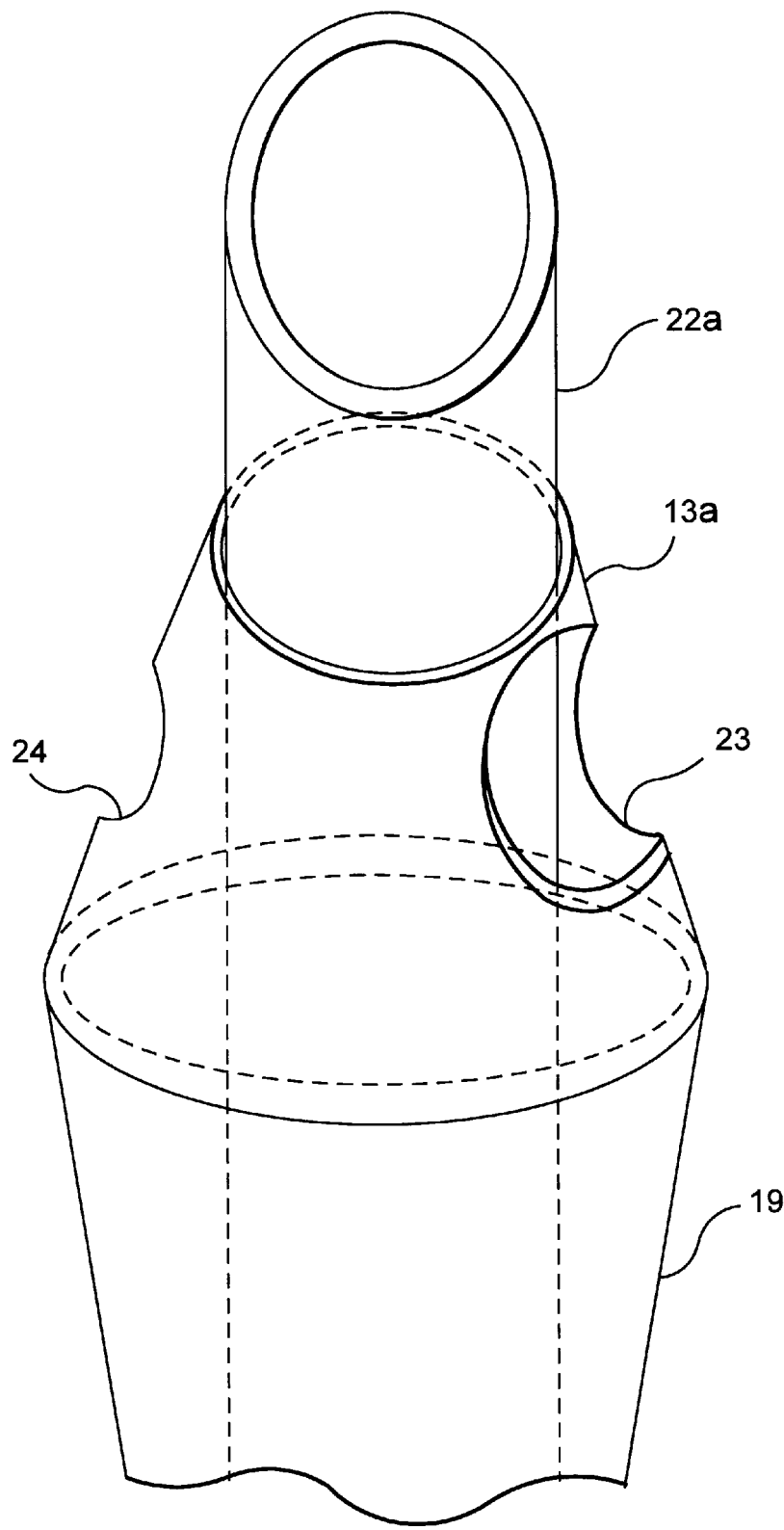
FIG. 8 is an enlarged view of the forward portion of a tip and shaped sleeve.

FIG. 8 shows a forward portion 22a of a tip 22 and the sleeve 19 which includes a distal end 13a and a pair of outlet passages 23 and 24 for delivering fluid into the incision adjacent the tip. The sleeve 19 is of the arched design, though this distal end configuration is preferably used with each shaped sleeve, in accordance with the present invention.

The non-circular infusion sleeve of the present invention is preferably made of a soft flexible material such as medical grade silicone, preferably having a uniform wall thickness. No ribs, grooves or granular surface are necessary or desirable, as these necessitate increased manufacturing cost, add complexities and complicate the force distributing properties of the non-circular infusion sleeve. While silicone sleeves have been used previously, these have been of circular cross-sections which have caused collapse and such sleeves have been considered to be unsatisfactory for this type of instrument. The applicant has discovered that the provision of sleeves having particular shapes of non-circular cross-section have the ability to limit the amount of deformation so as to avoid the problems encountered in the prior art, i.e., heating of the sleeve through contact with a vibrating needle, while at the same time allowing sufficient flexibility to enhance sealing with the adjacent tissue.

It can thus be seen that the instrument of the present invention eliminates wound incision leakage and heating enabling a cataract to be removed safely and properly. Further, since only a single soft sleeve as opposed to a dual sleeve design is used, the incision size can be minimized without restricting manipulation of the needle within the incision. By the elimination of undesired heat generation, and the maintenance of proper inflation pressure, the applicant's invention thus represents a significant advance in the art.

While preferred embodiments of the present invention have been shown and described it will be understood by those skilled in the art that various changes or modifications could be made without varying from the spirit and scope of the present invention.

What is claimed is:

1. A surgical instrument for removing issue through an incision in a patient's eye, the instrument including a handpiece, a hollow vibratable needle connected to the handpiece, an ultrasonic drive associated with the needle for imparting vibration thereto, the surgical instrument further comprising:

a hollow non-circular flexible infuision sleeve having a proximal portion and a distal portion, the proximal portion connected to the handpiece, the infuision sleeve surrounding a substantial portion of the vibratable needle, the infusion sleeve being co-axial therewith, a fluid passage defined between an outer surface of the needle and an inner wall surface of the sleeve, the distal end of the sleeve providing a port for delivery of the fluid adjacent a tip of the needle, the infusion sleeve having a shape defined by a non-circular cross-section having at least two constricting points, the non-circular shape being deformable to approximate a shape of the incision, the constriction points restricting deformation to prevent collapse of the sleeve onto the vibrating needle.

2. The surgical instrument of claim 1, wherein the shaped infusion sleeve has an uncompressed shape of a triangle having three constricting points.

3. The surgical instrument of claim 1, wherein the shaped infusion sleeve has a diamond shape with four constricting points.

4. The surgical instrument of claim 1, wherein the shaped infusion sleeve has an arched shaped with two constricting points.

5. The surgical instrument of claim 1, wherein the shaped infusion sleeve is made of silicone.

6. A method for removing tissue through an incision in a patient's eye comprising:

providing a surgical instrument having a handpiece, a hollow vibratable needle connected to the handpiece, an ultrasonic drive associated with the needle for imparting vibration thereto;

placing a hollow non circular flexible infusion sleeve over the needle;

the hollow non-circular flexible infusion sleeve having a proximal portion and a distal portion, the proximal portion connected to the handpiece, the infusion sleeve surrounding a substantial portion of the vibratable needle, the infusion sleeve being co-axial therewith, a fluid passage defined between an outer surface of the needle and an inner wall surface of the sleeve, the distal end of the sleeve providing a port for delivery of the fluid adjacent a tip of the needle, the infusion sleeve having a shape defined by a non-circular cross-section having at least two constricting points, the non-circular shape being deformable to approximate a shape of the incision, the constriction points restricting deformation to prevent collapse of the sleeve onto the vibrating needle;

making an incision in the eye; and placing the surgical instrument with the infusion sleeve into the incision and removing tissue therewith.

7. The method of claim 6, wherein the shaped infusion sleeve has an uncompressed shape of a triangle having three constricting points.

8. The method of claim 6, wherein the shaped infusion sleeve has a diamond shape with four constricting points.

9. The method of claim 6, wherein the shaped infusion sleeve has an arched shaped with two constricting points.

10. The method of claim 6, wherein the shaped infusion sleeve is made of silicone.

* * * * *